United States Patent
Tani et al.

(10) Patent No.: US 9,585,718 B2
(45) Date of Patent: Mar. 7, 2017

(54) MEDICAL TREATMENT DEVICE FOR HOLDING, COAGULATING, AND CUTTING LIVING TISSUE

(75) Inventors: Tohru Tani, Otsu (JP); Shigeyuki Naka, Otsu (JP)

(73) Assignee: NATIONAL UNIVERSITY CORPORATION SHIGA UNIVERSITY, Otsu-shi, Shiga (JP)

(*) Notice: Subject to any disclaimer, the term of this patent is extended or adjusted under 35 U.S.C. 154(b) by 473 days.

(21) Appl. No.: 13/519,110

(22) PCT Filed: Dec. 28, 2010

(86) PCT No.: PCT/JP2010/073752
§ 371 (c)(1),
(2), (4) Date: Jun. 25, 2012

(87) PCT Pub. No.: WO2011/081196
PCT Pub. Date: Jul. 7, 2011

(65) Prior Publication Data
US 2012/0259330 A1    Oct. 11, 2012

(30) Foreign Application Priority Data
Dec. 28, 2009  (JP) ............... 2009-297031

(51) Int. Cl.
A61B 18/18    (2006.01)
A61B 18/14    (2006.01)
A61B 18/00    (2006.01)

(52) U.S. Cl.
CPC ...... *A61B 18/1815* (2013.01); *A61B 18/1445* (2013.01); *A61B 2018/00589* (2013.01); *A61B 2018/00601* (2013.01)

(58) Field of Classification Search
CPC ...... A61B 18/1815; A61B 2018/00589; A61B 2018/00601; A61B 18/18; A61B 18/1445

(Continued)

(56) References Cited

U.S. PATENT DOCUMENTS 7,270,664 B2 *  9/2007  Johnson et al. ............. 606/51
2002/0128649 A1 *  9/2002  Bacher .............. A61B 18/1445
                                                                606/46

(Continued)

FOREIGN PATENT DOCUMENTS

JP    01-232948    9/1989
JP    2007-282666  11/2007

*Primary Examiner* — Christopher D Koharski
*Assistant Examiner* — Jeremiah Kimball
(74) *Attorney, Agent, or Firm* — Don D. Cha; Hamilton DeSanctis & Cha, LLP.

(57) ABSTRACT

In order to reliably cut off a living tissue by using a microwave in a surgical operation without causing excessive damage to the living tissue or without bleeding, it is necessary to suppress energy attenuation until the microwave reaches electrode blades for nipping, coagulating, and cutting off a tissue. However, it is difficult to suppress the energy attenuation. The present invention relates to a medical treatment device capable of reliably cutting off a living tissue by using a microwave while sealing vasculature by coagulating the living tissue without excessively damaging the living tissue. Specifically, the present invention relates to a medical treatment device including a movable first electrode blade connected to an external conductor and a fixed second electrode blade connected directly to a central electrode. The medical treatment device has a function of holding a living tissue between the movable first electrode blade and the fixed second electrode blade, coagulating the living tissue by supplying a microwave from the fixed second electrode blade, and cutting off the living tissue by turning the movable first electrode blade. In the medical treatment device, a turning mechanism for the movable first electrode blade is arranged at a certain clearance from the central electrode.

6 Claims, 5 Drawing Sheets

(58) Field of Classification Search
USPC .................................. 607/33, 37, 50–52, 45
See application file for complete search history.

(56) References Cited

U.S. PATENT DOCUMENTS

| | | | |
|---|---|---|---|
| 2007/0106295 A1* | 5/2007 | Garrison et al. | 606/50 |
| 2008/0243177 A1* | 10/2008 | Oren et al. | 606/210 |
| 2009/0012520 A1* | 1/2009 | Hixson | A61B 18/1445 606/51 |
| 2010/0023001 A1 | 1/2010 | Hosaka et al. | |
| 2012/0330310 A1* | 12/2012 | Takashino | 606/45 |

* cited by examiner

MEDICAL TREATMENT DEVICE FOR HOLDING, COAGULATING, AND CUTTING LIVING TISSUE

FIELD OF THE INVENTION

The present invention relates to a medical treatment device including blades movable relative to each other for holing, coagulating, and cutting off a living tissue.

BACKGROUND OF THE INVENTION

There are known surgical treatment devices using microwaves so as to perform coagulation, hemostasis, incision, and the like with respect to body parts such as digestive organs, the liver, the bladder, the prostate, the uterus, blood vessels, and the intestinal canal.

Specifically, a conventional electrosurgical knife or the like uses Joule heat generated by using a high-frequency voltage at a frequency of approximately 500 kHz so as to heat and coagulate a surface of a living tissue. When the coagulation is performed with such a conventional electrosurgical knife or the like using Joule heat, a living tissue is easily coagulated, and hence the coagulated surface may be peeled off and dropped from the living tissue.

Meanwhile, when a microwave is applied to a living tissue between electrodes, dielectric heat is generated in the living tissue by a near electromagnetic field formed by microwave power. The dielectric heat evaporates moisture of the living tissue, and the living tissue is coagulated and fixed. In this way, a vascular vessel is sealed, and a hemostatic effect is achieved.

When coagulation and hemostasis are performed by using microwaves, the living tissue can be coagulated at a relatively low temperature. Thus, the living tissue can be kept in a fixed state in which a function of the living tissue is stopped while maintaining a cell shape of the living tissue. Thus, a situation that the coagulated surface is peeled off or dropped from the living tissue is prevented.

Japanese Patent Application No. JP 2005-21658 A and Japanese Patent Application No. JP 2007-282666 A each disclose a device which uses microwaves as described above so as to perform coagulation, hemostasis, incision, and the like with respect to a living tissue. Treatment using microwaves involves a problem of a spark that may be generated by electrodes brought into contact with each other. The spark causes excessive damage to a living tissue. As a countermeasure, the medical treatment device disclosed in Japanese Patent Application No. JP 2007-282666 A is designed to prevent generation of the spark by preventing two electrodes from being brought into contact with each other at the time of holding a living tissue so as to maintain a parallel state therebetween. However, in the medical treatment device disclosed in Japanese Patent Application No. JP 2007-282666 A, a turning shaft of an electrode and a point of effort (position at which electrode open/close rod is mounted) exist in the same electrode, and a distance therebetween is small. Thus, the electrode cannot be lightly turned, and hence delicate work during a surgical operation is not easy. Further, a lower blade electrode connected to a central electrode is close to a conductive holder connected to an external conductor, and a distance from a distal end portion of coaxial cables to blades for cutting off a living tissue is long. Thus, there is a problem that a microwave is not efficiently applied to a living tissue.

SUMMARY OF THE INVENTION

Technical Problem

In order to reliably cut off a living tissue by using a microwave without bleeding, it is necessary to suppress energy attenuation until the microwave reaches electrode blades for nipping, coagulating, and cutting off a tissue. However, it is difficult to suppress the energy attenuation. It is therefore an object of the present invention to provide a medical treatment device capable of cutting off a living tissue reliably by suppressing attenuation during transmission of a microwave and safely coagulating the living tissue by efficiently applying the microwave to the living tissue by while preventing leakage of the microwave (electrical leakage) to an external conductor or another conductor connected thereto. Further, it is another object of the present invention to provide a medical treatment device capable of more reliably cutting off a living tissue by preventing short-circuiting in a structure of a turning portion of an electrode and facilitating mechanical movement thereof.

Solution to Problem

The inventors of the present invention diligently reviewed the above-mentioned problem, and found constructions made to solve the above-mentioned problem. Thus, the present invention has been attained.

That is, the present invention includes the following items:

1. A medical treatment device, including:
   a coaxial cable for transmitting a microwave;
   a fixed second electrode blade provided on a front side of a distal end of the coaxial cable and connected directly to a central electrode;
   a movable first electrode blade connected to an external conductor, the movable first electrode blade being turnable about a turning shaft and facing the fixed second electrode blade; and
   an electrode open/close rod,
   in which a clearance from a center of the distal end of the coaxial cable to a blade root portion of each of the movable first electrode blade and the fixed second electrode blade is equal to or larger than a radius of the coaxial cable,
   in which a clearance from a central electrode coupling portion to an external conductor coupling portion is equal to or larger than the radius of the coaxial cable, and
   in which the medical treatment device is configured to:
   hold a living tissue between the movable first electrode blade and the fixed second electrode blade;
   coagulate the living tissue by supplying a microwave from the fixed second electrode blade; and
   cut off the living tissue by turning the movable first electrode blade.

2. A medical treatment device according to the above-mentioned item 1, further including an insulating portion provided between the coaxial cable and the fixed second electrode blade.

3. A medical treatment device according to the above-mentioned item 2, in which the insulating portion has a length equal to or larger than the radius of the coaxial cable.

4. A medical treatment device according to any one of the above-mentioned items 1 to 3, in which an edge line of the movable first electrode blade and an edge line of the fixed second electrode blade are parallel to each other.

5. A medical treatment device according to the above-mentioned items 1 to 4, further including an insulator bonded to one surface of the fixed second electrode blade.

6. A medical treatment device according to any one of the above-mentioned items 1 to 5, in which the turning shaft of the movable first electrode blade is set on the movable first electrode blade side with respect to a center line of the edge line of the movable first electrode blade and the edge line of the fixed second electrode blade, and in which an electrode open/close rod connecting point is set on the fixed second electrode blade side with respect to the center line of the edge line of the movable first electrode blade and the edge line of the fixed second electrode blade.

7. A medical treatment device according to the above-mentioned item 6, in which a distance between the turning shaft of the movable first electrode blade and the electrode open/close rod connecting point is equal to or larger than the radius of the coaxial cable.

8. A medical treatment device according to the above-mentioned item 6 or 7, further including coupling means for coupling the turning shaft and the electrode open/close rod connecting point to each other.

9. A medical treatment device according to any one of the above-mentioned items 1 to 8, in which the movable first electrode blade and the fixed second electrode blade are coated so as to prevent adhesion of a coagulated tissue.

Advantageous Effects of Invention

When the fixed second electrode blade is connected directly to the central electrode so as to reduce the clearance between the distal end of the coaxial cable and the movable first electrode blade and the fixed second electrode blade for cutting off a living tissue, a microwave is efficiently supplied to the fixed second electrode blade without attenuation. In this case, when a turning mechanism for the movable first electrode blade is arranged at a certain clearance from the central electrode, the microwave is efficiently supplied to the fixed second electrode blade without attenuation. In other words, with a structure in which a certain clearance or more is maintained between an exposed part of the central electrode, for example, to the external conductor including the movable first electrode blade, the microwave does not leak to the external conductor or the like before the microwave reaches the living tissue. Thus, the microwave can be more efficiently applied. When the microwave is efficiently applied, treatment can be performed with lower electricity, and hence risk of a spark or the like can be avoided. Further, when the turning shaft and the electrode open/close rod connecting point are positioned as in the invention of the present application, the movable first electrode blade is more easily turned, and hence a living tissue is easily held between the movable first electrode blade and the fixed second electrode blade. In addition, after coagulation and sealing of vasculature are performed by using a microwave, the movable first electrode blade is more easily turned, and hence the living tissue is more reliably cut off.

BRIEF DESCRIPTION OF DRAWINGS

FIG. 2(A) illustrates the medical treatment device of the present invention, in which an insulating portion is not provided between the coaxial cable and the electrode blades, and FIG. 2(B) illustrates the medical treatment device of the present invention, in which the insulating portion is provided between the coaxial cable and the electrode blades.

FIG. 4(A) illustrates the medical treatment device of the present invention, in which the insulating portion is not provided between the coaxial cable and the electrode blades, and FIG. 4(B) illustrates the medical treatment device of the present invention, in which the insulating portion is provided between the coaxial cable and the electrode blades.

FIG. 5(A) illustrates a state in which blade edges are opened. FIG. 5(B) illustrates a state in which the edge lines are parallel to each other. FIG. 5(C) illustrates a state in which the blade edges are closed.

FIG. 6(A) illustrates the medical treatment device of the present invention, in which the insulating portion is not provided between the coaxial cable and the electrode blades, and FIG. 6(B) illustrates the medical treatment device of the present invention, in which the insulating portion is provided between the coaxial cable and the electrode blades.

DESCRIPTION OF EMBODIMENT

A medical treatment device according to the present invention includes a fixed second electrode blade connected directly to a central electrode on a front side of a distal end of a coaxial cable for transmitting a microwave, and a movable first electrode blade which is capable of facing the fixed second electrode blade and connected to an external conductor. This part is collectively referred to as an electrode portion. In accordance with a reciprocation of an electrode open/close rod, the movable first electrode blade turns about a turning shaft so as to face the fixed second electrode blade provided on the front side of the distal end of the coaxial cable. The turning shaft of the movable first electrode blade is positioned on a surface of the external conductor at a certain clearance from the central electrode. The turning shaft electrically couples the movable first electrode blade to the external conductor.

Through turning of the movable first electrode blade, a living tissue is held between the movable first electrode blade and the fixed second electrode blade. Through supply of a microwave from the fixed second electrode blade, the living tissue is coagulated, and vasculature is sealed. Then, through further turning of the movable first electrode blade, the living tissue is cut off.

A microwave is transmitted to the central electrode and the fixed second electrode blade. Thus, when the external conductor or an electrical conductor connected thereto is close to the central electrode or the fixed second electrode blade, leakage of the microwave (electrical leakage) to the external conductor and the like occurs. In the medical treatment device of the present invention, the external conductor, the electrical conductor connected thereto, and the movable first electrode blade are arranged at certain clearances from the central electrode. Thus, attenuation of the microwave to be applied to the living tissue, which is caused by leakage, is suppressed.

Figure 8:
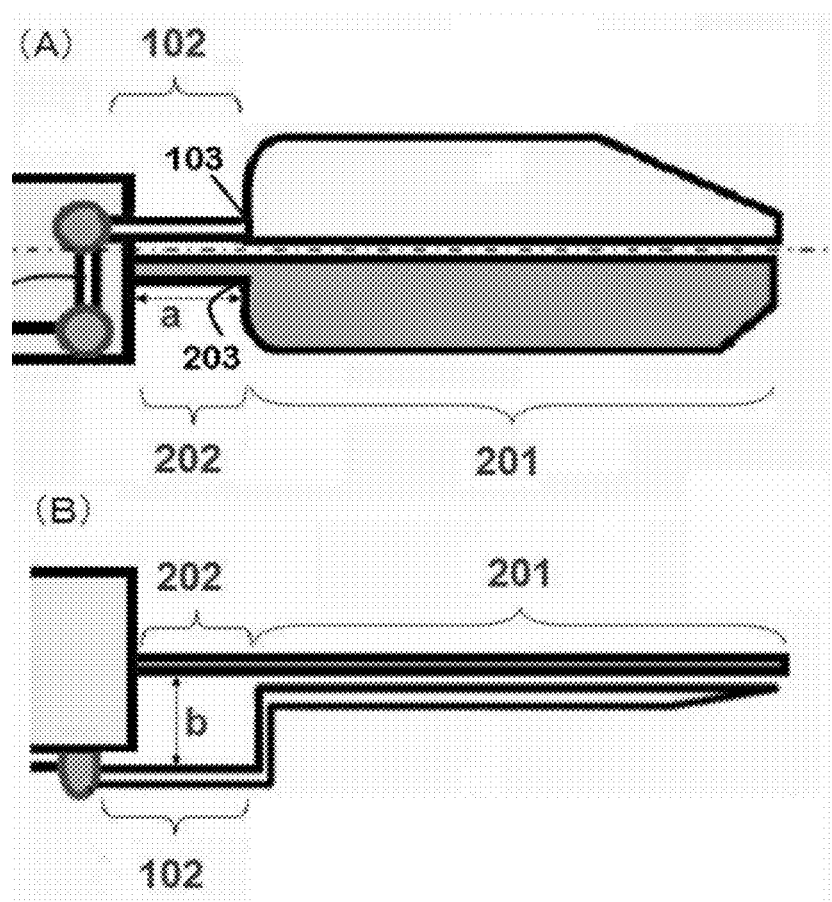
FIG. 8 each illustrate a movable first electrode blade, an external conductor coupling portion, a fixed second electrode blade, and a central electrode coupling portion, in each of which reference symbol "a" represents a clearance from a center of a distal end of the coaxial cable to a blade root portion of each of the electrode blades, and reference symbol "b" represents a clearance from the central electrode coupling portion to the external conductor coupling portion.

In the medical treatment device of the present invention, the movable first electrode blade is electrically connected to the external conductor by the turning shaft. An external conductor coupling portion (102) refers to a coupling portion between the movable first electrode blade (101) and the turning shaft. The fixed second electrode blade (201) is connected directly to the central electrode. In the present invention, a clearance from a center of the distal end of the coaxial cable to a blade root portion (103,203) of each of the electrode blades (clearance "a" in FIG. 8(A)) is equal to or larger than a radius of the coaxial cable, and a clearance from a central electrode coupling portion (202) to the external conductor coupling portion (102) (clearance "b" in FIG. 8(B)) is equal to or larger than the radius of the coaxial cable. The central electrode coupling portion (202) refers to a coupling portion ranging from the distal end of the coaxial cable to the blade root portion (103,203) of the fixed second electrode blade (201). The blade root portion refers to a part of each of the electrode blades having a function of cutting off a living tissue, which is closest to the coaxial cable. The clearance from the center of the distal end of the coaxial cable to the blade root portion of each of the electrode blades and the clearance from the central electrode coupling portion to the external conductor coupling portion are preferably equal to or larger than the radius of the coaxial cable and three times or less as large as the radius of the coaxial cable, more preferably equal to or larger than the radius of the coaxial cable and equal to or smaller than a diameter of the coaxial cable. When those clearances are equal to or smaller than the radius of the coaxial cable, the microwave leaks. When those clearances are more than three times as large as the radius of the coaxial cable, transmission efficiency of the microwave is deteriorated. In addition, strength of the blades and a nipping force decrease.

Each of the electrode blades is a part having a structure of a blade for cutting off a living tissue, and has a large width. A size of the blade varies depending on usage and intended use. For example, for open operations, the blade has a length of from 2 mm to 50 mm, preferably from 5 mm to 30 mm, and has a width of from 0.5 mm to 3 mm, preferably from 1 mm to 2 mm. The external conductor coupling portion is positioned between the external conductor and the movable first electrode blade, and parallel to the central electrode coupling portion. The external conductor coupling portion is not limited in shape, and may be formed, for example, into an elongated shape or a plate-like shape.

In the structure according to the present invention, the distal end of the coaxial cable and the electrode blades are positioned close to each other. However, certain clearances are maintained between the central electrode at a central portion of a terminal end of the coaxial cable and the movable first electrode blade, between the external conductor coupling portion and the central electrode coupling portion, between the fixed second electrode blade and the external conductor, and between the fixed second electrode blade and the external conductor coupling portion. In addition, only the movable first electrode blade can be brought close to the fixed second electrode blade. Thus, energization of the external conductor via the central electrode or the fixed second electrode blade remains interrupted unless a living tissue is held between both the blades. With this, a microwave can be efficiently applied to the nipped living tissue, and a risk of a spark can be avoided. As a result, treatment can be safely performed with lower electricity.

According to the medical treatment device of the present invention, a living tissue can be held between the movable first electrode blade and the fixed second electrode blade. It is preferred that the living tissue be nipped and held between the movable first electrode blade and the fixed second electrode blade in a manner that the fixed second electrode blade comes into contact with the living tissue and then the movable first electrode blade turns. In a preferred embodiment, the movable first electrode blade turns so as to secure a state in which an edge line of the movable first electrode blade and an edge line of the fixed second electrode blade are spaced apart from each other at a certain interval and to hold the living tissue in the certain interval between both the blades. It is more preferred that the edge line of the movable first electrode blade and the edge line of the fixed second electrode blade be secured to be parallel to each other so that the living tissue can be held in an interval therebetween.

The fixed second electrode blade according to the invention of the present application is connected directly to the central electrode, and hence a microwave is efficiently supplied from the central electrode. When a microwave is fed under a state in which a living tissue is held by the movable first electrode blade and the fixed second electrode blade, the microwave is applied from the fixed second electrode blade to the living tissue. Then, the movable first electrode blade is energized via the living tissue, and the microwave flows into the external conductor. It is preferred that the microwave be supplied to the fixed second electrode blade after the living tissue is held between the movable first electrode blade and the fixed second electrode blade.

When a microwave is supplied from the fixed second electrode blade under the state in which a living tissue is held between the fixed second electrode blade and the movable first electrode blade positioned parallel thereto, dielectric heat is generated in the living tissue by a near electromagnetic field formed between the movable first electrode blade and the fixed second electrode blade by microwave power. The living tissue is coagulated by the dielectric heat, with the result that the vasculature is sealed. Then, when the movable first electrode blade is further turned in a state of the coagulation treatment, the movable first electrode blade and the fixed second electrode blade come closer to each other from their blade edges, and intersect with each other. In this way, the living tissue is sheared. The movable first electrode blade and the fixed second electrode blade come closer to each other from their blade edges, and hence the living tissue held therebetween can be sheared without being dropped off from between the blades.

When the movable first electrode blade and the fixed second electrode blade are excessively close to each other, a spark is generated to cause excessive damage to the living tissue. Further, when a part of the fixed second electrode blade comes into contact with the living tissue under a state in which the movable first electrode blade and the living tissue are held in contact with each other, a microwave concentrates on that one point of the blade, and excessive electricity is generated. As a result, a spark is generated by excessive electricity to cause excessive damage to the living tissue. In order to avoid the spark, the edge line of the movable first electrode blade and the edge line of the fixed second electrode blade are maintained to be spaced apart from each other at a certain interval. In addition, the microwave is supplied after the living tissue to be coagulated and cut off is stably held in the clearance. Thus, the living tissue is coagulated and cut off without causing excessive damage to the living tissue.

The clearance to be maintained between the movable first electrode blade and the fixed second electrode blade ranges preferably from 0.5 mm to 20 mm, more preferably from 1 mm to 15 mm, further preferably from 2 mm to 10 mm. When the clearance is maintained, the movable first electrode blade and the fixed second electrode blade do not come into electrical contact with each other until an open state of the movable first electrode blade is switched to the parallel state. Thus, the spark to be caused by the contact or approach of the electrodes is not generated, and the living tissue can be stably held.

Both the electrodes can be formed into shapes for known purposes as long as the function of holding, the function of coagulation, and the function of cutting off a living tissue are exerted. Thus, both the electrodes are not particularly limited in shape. Parts of the electrodes, which come into contact with a living tissue, can be formed into various shapes such as a substantially linear shape, a curved shape, and a projection-recess shape. Each of the electrodes is formed of a general conductor, specifically, made of gold-plated or sliver-plated copper, gold-plated or sliver-plated brass, a copper alloy such as phosphor bronze, or the like. It is more suitable for the electrodes to be coated so as to prevent adhesion of a coagulated tissue at the time when the electrodes are held in contact with a living tissue. Such coating is performed with use of gold, a Teflon (trademark) based material, and the like. With this, without adhesion of a coagulated living tissue, coagulation treatment and cutting treatment can be performed in series.

Figure 2:
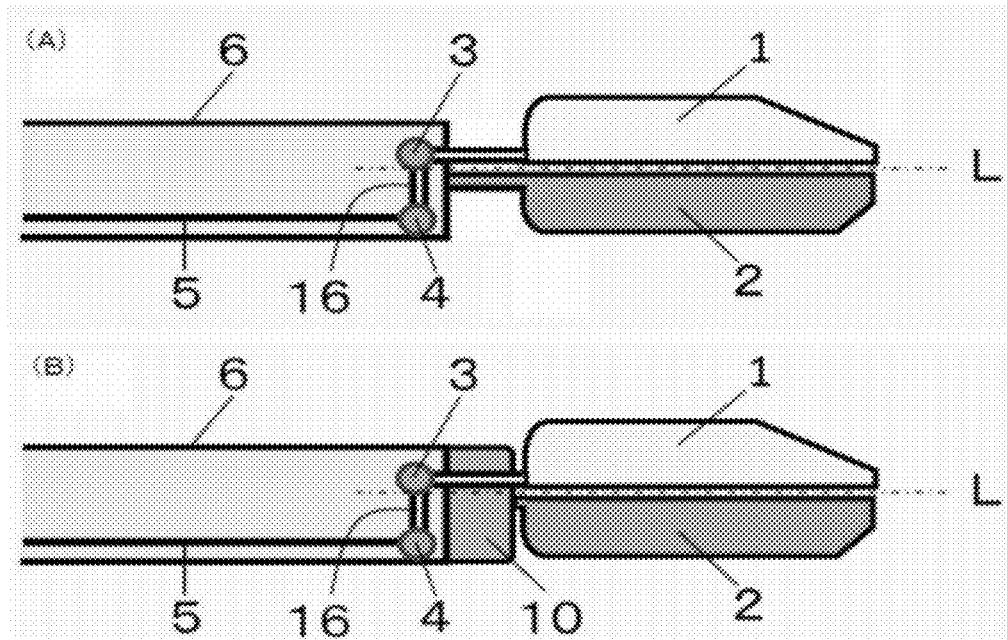
FIG. 2 are each a side view of a coaxial cable, an electrode open/close rod, and an electrode portion set inside a distal end part of an outer cylindrical tube of the medical treatment device of the present invention, in each of which the line L indicates a center line of an edge line of a movable first electrode blade and an edge line of a fixed second electrode blade.
Figure 3:
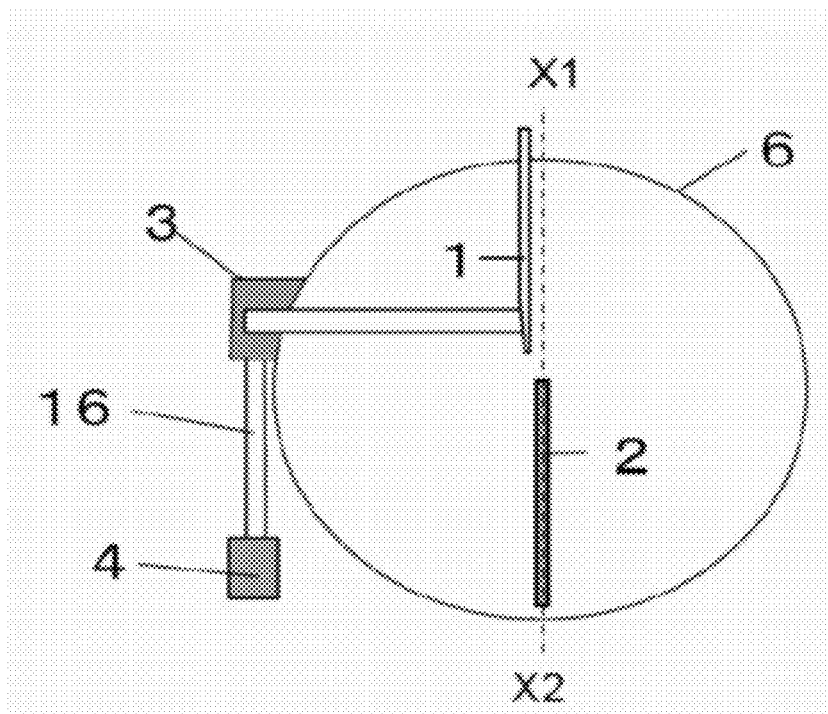
FIG. 3 is a front view of the medical treatment device of the present invention in a state of FIGS. 2.

In the medical treatment device according to the present invention, the turning shaft of the movable first electrode blade is set on the movable first electrode blade side and an electrode open/close rod connecting point is set on the fixed second electrode blade side with respect to a center line of the edge line of the movable first electrode blade and the edge line of the fixed second electrode blade. As indicated by the line L in FIG. 2, the center line of the edge line of the movable first electrode blade and the edge line of the fixed second electrode blade is a line positioned at a center of the edge line of the movable first electrode blade and the edge line of the fixed second electrode blade. The description "the turning shaft of the movable first electrode blade is set on the movable first electrode blade side with respect to the center line" refers to a state in which, when the movable first electrode blade and the fixed second electrode blade are observed in side view as illustrated in FIG. 2, the turning shaft of the movable first electrode blade is set on the movable first electrode blade with respect to the center line. The description "an electrode open/close rod connecting point is set on the fixed second electrode blade side with respect to the center line" refers to a state in which, when the movable first electrode blade and the fixed second electrode blade are similarly observed in side view as illustrated in FIG. 2, the electrode open/close rod connecting point is positioned on the fixed second electrode blade side with respect to the center line. The electrode open/close rod connecting point refers to a point through which a reciprocation of the electrode open/close rod is transmitted as a turning force for the movable first electrode blade, that is, a point of action of the force of the reciprocation.

In the medical treatment device according to one preferred embodiment of the present invention, a distance between the turning shaft of the movable first electrode blade and the electrode open/close rod connecting point is equal to or larger than the radius of the coaxial cable. The electrode open/close rod connecting point and the turning shaft are coupled to each other by coupling means. With this, a force applied to the electrode open/close rod connecting point is transmitted to the turning shaft so as to turn the movable first electrode blade. In this case, the movable first electrode blade can be turned with a smaller force as the distance between the electrode open/close rod connecting point and the turning shaft is larger.

The distance between the turning shaft and the electrode open/close rod connecting point refers to a linear distance between the turning shaft and the electrode open/close rod connecting point. The coupling means for coupling the turning shaft and the electrode open/close rod connecting point to each other is not particularly limited, and may be formed of a plate-like member, a bar-like member, a linear member, and the like. As the coupling means, there are exemplified a single electrode plate, a plate separated from the electrodes, a coupling rod, and a coupling wire. A combination of the coupling rod and the coupling wire, which has rigidity, is suitable.

For example, a connecting plate may be planar, and a bar may be linear. Alternatively, the connecting plate or the bar may be curved along an outer periphery of the coaxial cable. The turning shaft is connected to the coaxial cable and electrically connected to the external conductor. The distance between the turning shaft and the electrode open/close rod connecting point is preferably equal to or larger than the radius of the coaxial cable and equal to or smaller than the diameter of the coaxial cable. When the distance is equal to or larger than the radius of the coaxial cable, the movable first electrode blade can be turned with a smaller force. When the distance is larger than the diameter of the coaxial cable, there arise problems such as difficulty in housing the coaxial cable into the outer cylindrical tube.

The electrode open/close rod connecting point may be provided together with the turning shaft on the same circumference, or may be provided on the distal end side or a rear side of the coaxial cable with respect to the position on the same circumference.

The coaxial cable has a function of transmitting a microwave from a microwave source via a connector portion to the fixed second electrode blade. The coaxial cable is formed of the central electrode as an electrical conductor made, for example, of phosphor bronze, a shield tube as an insulator made, for example, of Teflon (trademark), for covering the central electrode, and a ground pipe as an external conductor (electrical conductor) made, for example, of brass. An outside of the coaxial cable may be covered with a shield holder (also referred to as guide tube). The shield holder is preferred to be made of a non-conductive material (for example, Teflon (trademark), or formed of a non-magnetic coil made of phosphor bronze or the like).

The electrode open/close rod includes a flexible towing wire, and is protected by a flexible guide tube from frictional breakage. The flexible towing wire is formed of a rope of a non-magnetic metal wire made of phosphor bronze or the like, or made of carbon fiber or the like. The guide tube is made, for example, of Teflon (trademark), or formed of a non-magnetic coil made of phosphor bronze or the like.

An insulating portion may be provided between the coaxial cable and the fixed second electrode blade which are used in the present invention. The insulating portion covers the fixed second electrode blade so as to prevent leakage of the microwave. The insulating portion may be held in contact with or spaced apart from the distal end of the coaxial cable. When the insulating portion is provided, energization of the external conductor and the like via the central electrode or the fixed second electrode blade reliably remains interrupted unless a living tissue is directly held. With this, the microwave can be efficiently applied. A length of the insulating portion is not limited as long as the microwave is prevented from being leaked from the central electrode coupling portion to the external conductor or the like. The length of the insulating portion is suitably equal to or larger than the radius of the coaxial cable. The length of the insulating portion is more preferably equal to or larger than the radius of the coaxial cable and three times or less as large as the radius of the coaxial cable, further preferably equal to or larger than the radius of the coaxial cable and equal to or smaller than the diameter of the coaxial cable.

The insulating portion is preferred to be made of a non-conductive material (for example, Teflon (trademark), formed of a non-magnetic coil made of phosphor bronze or the like, or made of a polyether ether ketone resin).

In the medical treatment device according to the present invention, a microwave is transmitted via the coaxial cable up to a position close to the movable first electrode blade and the fixed second electrode blade, and the central electrode of the coaxial cable is connected directly to the fixed second electrode blade. A microwave applied with this structure can be efficiently transmitted. In particular, when the central electrode itself serves as the fixed second electrode blade, a microwave can be most efficiently transmitted to a living tissue.

In the medical treatment device according to another embodiment of the present invention, an insulator is bonded to one surface of the fixed second electrode blade. The one surface refers to a surface of the fixed second electrode blade on the movable first electrode blade side. A living tissue is held between the movable first electrode blade and the fixed second electrode blade having the insulator bonded thereto. Then, a microwave is supplied to the fixed second electrode blade so as to coagulate the living tissue. After that, the movable first electrode blade is turned to cut off the living tissue. The insulator moves integrally with the fixed second electrode blade, and is kept positioned between the movable first electrode blade and the fixed second electrode blade in a series of manipulation. The insulator is suitable to have a size covering one entire surface of the fixed second electrode blade or only a cutting edge part. The insulator and the fixed second electrode blade integrally form a blade. A material for the insulator is not limited as long as a function of the insulator is exerted, and may include a synthetic resin, a glass fiber, and pottery. Ceramics are preferred, and particularly, fine ceramics are suitable.

The medical treatment device according to the present invention includes a manipulating portion for moving fore and aft the electrode open/close rod. The manipulating portion refers to a portion for opening and closing the movable first electrode blade through conversion of movement caused by a manipulation of a pivotable, movable handle, such as holding, pulling, gripping, and turning, into fore-and-aft movement, and through transmission of the fore-and-aft movement to the electrode open/close rod. Specifically, a widely known mechanism such as a slider crank mechanism can be used, in which load is applied to a manipulating portion such as the movable handle so as to cause pivot movement and the pivot movement is converted into fore-and-aft movement to be transmitted to the electrode open/close rod. The manipulating portion includes, as a main component, a main body portion including, for example, a movable handle portion and a fixed handle portion, and includes the electrode open/close rod for transmitting movement of the movable handle as fore-and-aft movement into the fixed handle portion. Further, the manipulating portion may include an electrode manipulation adjusting portion for adjusting the fore-and-aft movement of the electrode open/close rod. The electrode manipulation adjusting portion has a function of adjusting turning of the movable first electrode blade, and for example, may be capable of adjusting the clearance between the edge line of the movable first electrode blade and the edge line of the fixed second electrode blade which are parallel to each other.

The medical treatment device according to the present invention includes the outer cylindrical tube which has a cylindrical tubular shape and serves as a part connecting the manipulating portion and the electrodes to each other. The outer cylindrical tube functions as a cover, and houses therein the electrode open/close rod and the coaxial cable for transmitting a microwave. A length of the outer cylindrical tube is not particularly limited as long as a sufficient length is secured for connecting a part to be manipulated by a manipulator and the electrode portion as apart to be brought into contact, for example, with a tissue subjected to a surgical operation. Normally, the length of the outer cylindrical tube ranges approximately from 5 cm to 50 cm. For abdominal operations, the length of the outer cylindrical tube ranges preferably from 5 cm to 20 cm, more preferably from 7 cm to 18 cm. For laparoscopic operations, the length of the outer cylindrical tube ranges preferably from 20 cm to 40 cm, approximately. The medical treatment device according to the present invention is preferred to be entirely made of a non-magnetic metal such as phosphor bronze. With this, even under a magnetic environment, for example, use in an MR system, the medical treatment device can be suitably used.

In the present invention, the electrode open/close rod refers to a manipulating shaft for transmitting the movement caused by the manipulating portion to the movable first electrode blade as fore-and-aft movement. Generally, the electrode open/close rod is formed of a wire, and transmits a force from the manipulating portion to the electrode portion. An outer side of the electrode open/close rod is suitable to be guided by the guide tube. In the present invention, a microwave at a frequency of from 900 MHz to 6,000 MHz can be equivalently used. A preferred frequency of the microwave is 2,450 MHz.

In the medical treatment device according to the present invention, the outer cylindrical tube and the electrode portion may be connected to each other by a bent holder. The bent holder has a length of substantially from 3 cm to 6 cm, and is bent at an angle of from 1 degree to 90 degrees, suitably from 5 degrees to 85 degrees. The bent holder may include a curved portion integrated with the outer cylindrical tube. Specifically, the bent holder sometimes refers to a holder formed of a single outer cylindrical tube in which a part near the distal end electrode, in other words, a neck portion is curved.

The bent holder has a cylindrical shape, and houses the coaxial cable that may be covered with the shield holder, and the electrode open/close rod that may be set in the guide tube. Each of the coaxial cable and the electrode open/close rod to be set in the bent holder has a curvature which is measured in the same direction as that in which the bent holder is curved and which is substantially the same as the angle of the bent holder.

The outer cylindrical tube and/or the bent holder of the medical treatment device according to the present invention can be freely turned, which enables a manipulator to easily perform upward, downward, and sideward operative treatment. For the turning, a turning element for turning the outer cylindrical tube and/or the bent holder may be provided at the connecting portion between the outer cylindrical tube and the manipulating portion.

Figure 1:
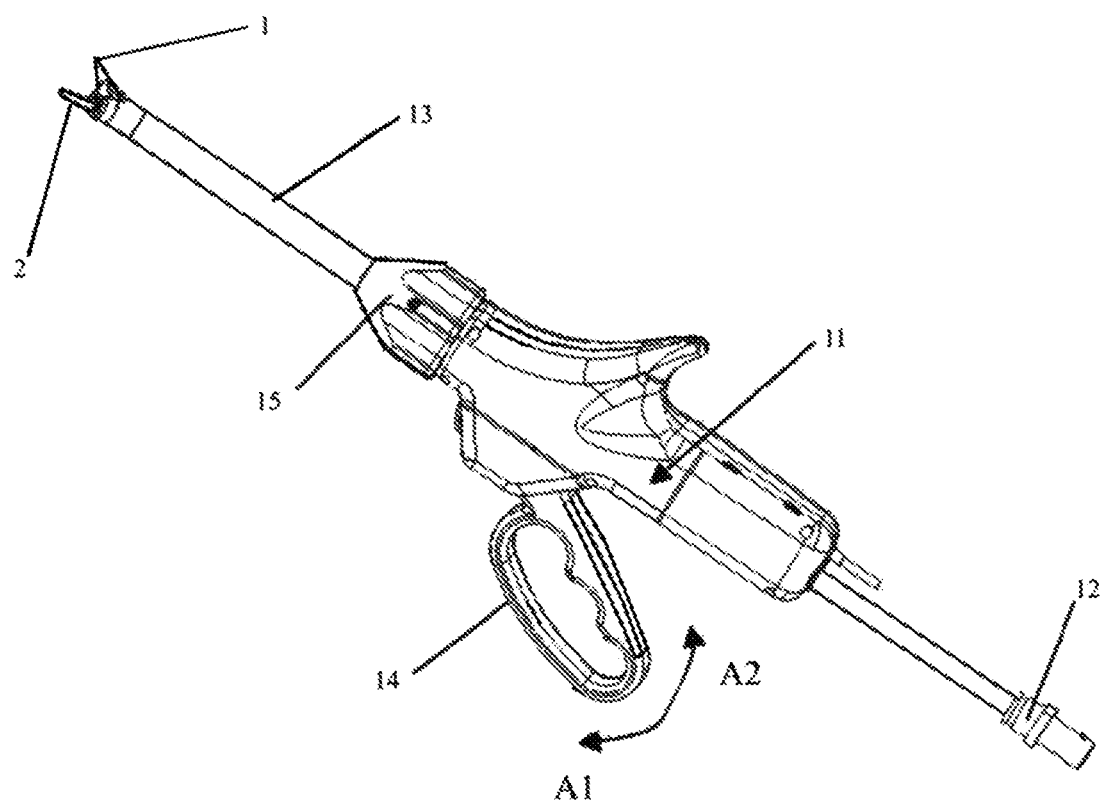
FIG. 1 illustrates an overall structure of a medical treatment device according to an embodiment of the present invention (reference view).

In the following, description is made of the embodiment of the present invention with reference to the drawings. FIG. 1 is a reference view, and FIGS. 2 to 8 illustrate features of the present invention.

FIG. 1 illustrates a medical treatment device according to an embodiment of the present invention. In FIG. 1, reference symbol 11 represents a main body portion. A connector 12 is arranged at a rear end of the main body portion 11. A microwave at a frequency of, for example, 2.45 GHz is supplied through the connector 12. An outer cylindrical tube 13 extends from the main body portion 11. The outer cylindrical tube 13 houses therein a coaxial cable 6 for transmitting microwave from the connector 12, and an electrode open/close rod 5 for opening and closing electrodes by transmitting movement of a movable handle 14 to a movable first electrode blade 1.

The movable handle 14 is pivotably mounted to a lower side of the main body portion 11. In the main body portion 11, there is provided a slider crank mechanism for converting the pivot movement of the movable handle 14 into fore-and-aft movement of the electrode open/close rod 5. Further, the main body portion 11 is provided with a turning element 15. Through turning of the turning element 15, the outer cylindrical tube 13 fixed to the turning element 15 can be turned at a desired angle.

As illustrated in FIG. 2, at a distal end of the outer cylindrical tube 13, the movable first electrode blade 1 and a fixed second electrode blade 2 are provided to face each other. The movable first electrode blade 1 is provided to be turnable about a turning shaft 3. When the movable handle 14 is pivoted, the electrode open/close rod 5 in the outer cylindrical tube 13 is moved fore and aft and generates a force. The force thus generated acts on an electrode open/close rod connecting point 4, and then causes the movable first electrode blade 1 to turn about the turning shaft 3. The microwave from the connector 12 is supplied to the fixed second electrode blade 2 via a central electrode 7 provided at a central portion of the coaxial cable 6.

Under a state in which a force is not applied to the movable handle 14, the movable handle 14 is urged in a direction of the arrow A1 in FIG. 1. At this time, as illustrated in FIG. 5(A), the movable first electrode blade 1 separates from the fixed second electrode blade 2, and a blade-edge open state is assumed. When the movable handle 14 is pivoted in a direction of the arrow A2, the electrode open/close rod 5 is moved in a direction of the arrow B2 illustrated in FIG. 5(B). As a result, the movable first electrode blade 1 and the fixed second electrode blade 2 come closer to each other. When the movable handle 14 is further pivoted in the direction of the arrow A2, the electrode open/close rod is further moved in the direction of the arrow B2. As a result, as illustrated in FIG. 5(C), the movable first electrode blade 1 comes closer to the fixed second electrode blade 2 from a blade edge side, and a blade-edge close state is assumed.

The medical treatment device according to the embodiment of the present invention is used as follows. First, the movable first electrode blade 1 and the fixed second electrode blade 2 are set in the blade-edge open state as illustrated in FIG. 5(A), and the movable first electrode blade 1 and the fixed second electrode blade 2 are guided to a subject living tissue. After the distal ends of the movable first electrode blade 1 and the fixed second electrode blade 2 are guided to the living tissue to be subjected to treatment, first, the fixed second electrode blade is brought into contact with the living tissue to be subjected to coagulation cutting, and then, the movable handle 14 is pivoted in the direction of the arrow A2. When the movable handle 14 is pivoted in the direction of the arrow A2, the movable first electrode blade 1 is closed. As a result, the living tissue can be held between the movable first electrode blade 1 and the fixed second electrode blade 2 in the blade-edge state illustrated in FIG. 5(B). The microwave is supplied from the fixed second electrode blade 2 while the living tissue is held as described above. With this, dielectric heat is generated in the living tissue by a near electromagnetic field formed between the movable first electrode blade 1 and the fixed second electrode blade 2 by microwave power, and the living tissue is coagulated by the dielectric heat. Then, the movable handle 14 is gripped with a greater force in the state of the coagulation treatment so that the movable handle 14 is further pivoted in the direction of the arrow A2. With this manipulation, the movable first electrode blade 1 and the fixed second electrode blade 2 are brought into the blade-edge close state as illustrated in FIG. 5(C). In this way, the living tissue is cut off by shearing.

As described above, through the manipulation of the movable handle 14 of the medical treatment device according to the embodiment of the present invention, as illustrated respectively in FIGS. 5(A) to 5(C), the blade-edge open state, the living-tissue holding state, and the blade-edge close state are assumed. With this configuration, the living tissue can be cut off by shearing in the following manner: holding the living tissue between the movable first electrode blade 1 and the fixed second electrode blade 2; coagulating the living tissue by applying a microwave between the movable first electrode blade 1 and the fixed second electrode blade 2, with the blade edges of the movable first electrode blade 1 and the fixed second electrode blade 2 being parallel to each other; and bringing the movable first electrode blade 1 and the fixed second electrode blade 2 into the blade-edge close state.

Further, the medical treatment device according to the embodiment of the present invention is entirely made of a non-magnetic metal such as phosphor bronze. With this, even under a magnetic environment, for example, use in an MR system, the medical treatment device can be suitably used.

Figure 4:
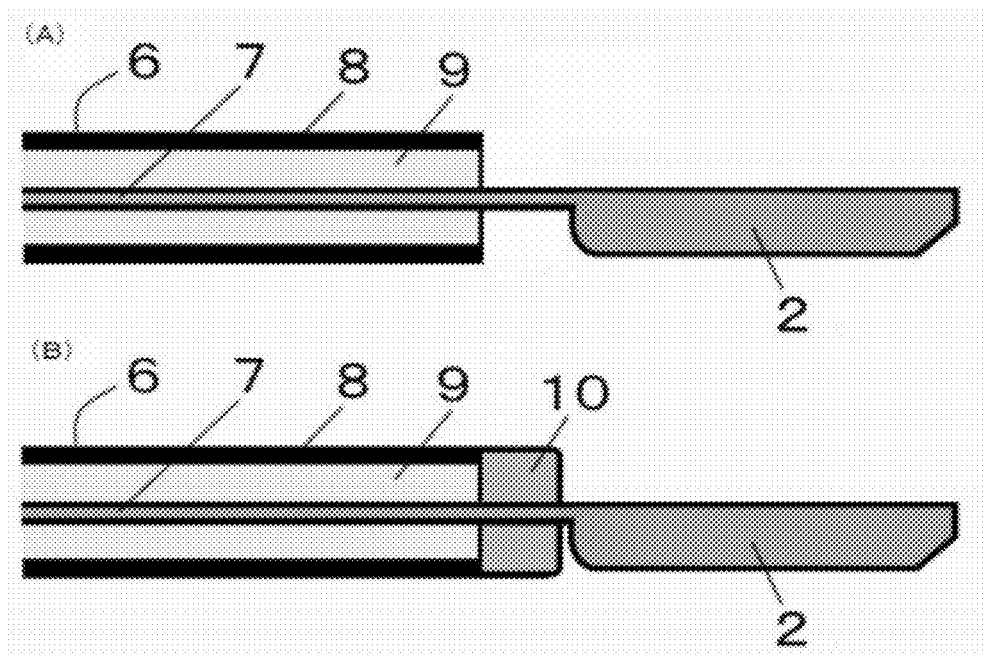
FIG. 4 are each a sectional view taken along the line X1-X2 of FIG. 3.

The outer cylindrical tube 13 houses therein the coaxial cable 6 and the electrode open/close rod 5 illustrated in FIGS. 2 to 8. The coaxial cable 6 is formed of the central electrode 7 as an electrical conductor made, for example, of phosphor bronze, an insulator 9 made, for example, of Teflon (trademark), for covering the central electrode 7, and a pipe (ground pipe) 8 as an external conductor (electrical conductor) made, for example, of brass (FIG. 4).

An insulating portion 10 made, for example, of a polyether ether ketone resin is fixed to a distal end of the coaxial cable 6, and the fixed second electrode blade 2 is fixed to the insulating portion 10. The fixed second electrode blade 2 is connected directly to the central electrode 7 of the coaxial cable 6. The insulating portion 10 has a thickness equal to or larger than a radius of the coaxial cable 6 and equal to or smaller than a diameter of the coaxial cable 6.

Figure 5:
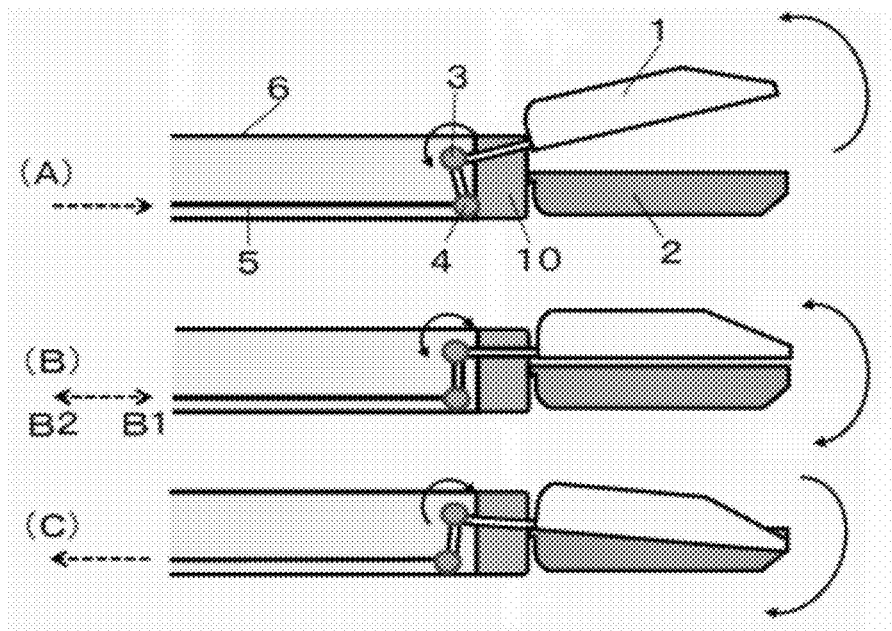
FIG. 5 are each a side view of the coaxial cable, the electrode open/close rod, and the electrode portion.
Figure 6:
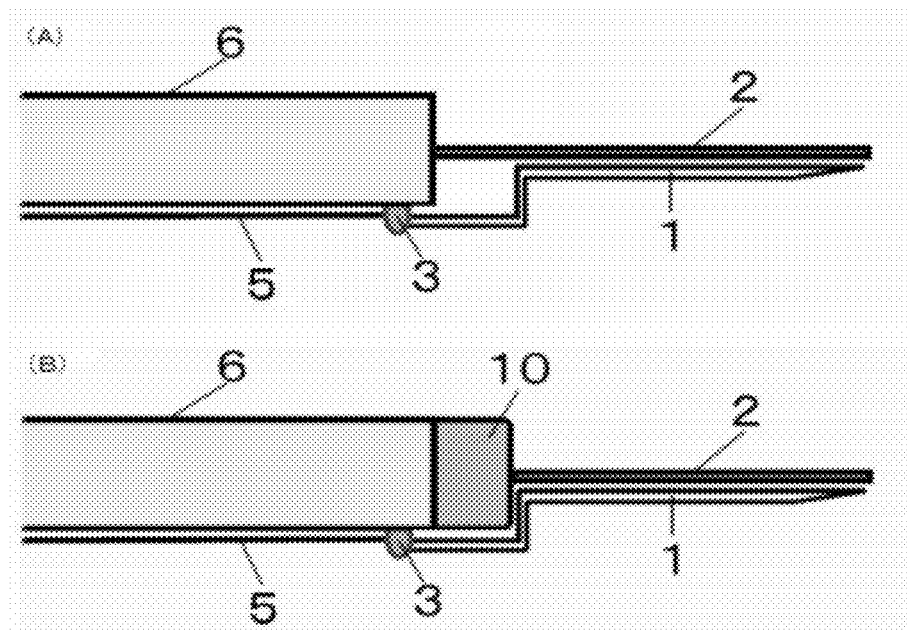
FIG. 6 are each a top view of the coaxial cable, the electrode open/close rod, and the electrode portion.
Figure 7:
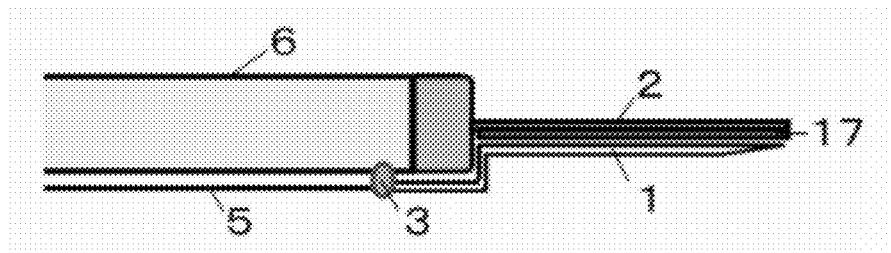
FIG. 7 is a top view of the coaxial cable, the electrode open/close rod, and the electrode portion of the medical treatment device of the present invention, in which an insulator is bonded to the fixed second electrode blade.

Meanwhile, as illustrated in FIGS. 2 and 5, the movable first electrode blade 1 is pivotally supported to be turnable by the turning shaft 3. Further, an end of the electrode open/close rod 5 is connected to the electrode open/close rod connecting point 4. A coupling rod 16 connects the electrode open/close rod connecting point 4 to the turning shaft 3. A distance between a center of the turning shaft 3 and a center of the electrode open/close rod connecting point 4 is set to be equal to or larger than the radius of the coaxial cable and equal to or smaller than the diameter of the coaxial cable.

Note that, the movable first electrode blade 1 and the fixed second electrode blade 2 are coated so as to prevent adhesion with use of a Teflon (trademark) based material, plated gold, and the like. Thus, without adhesion of a coagulated living tissue, coagulation treatment and cutting treatment can be performed in series.

The present invention is not limited to the above-mentioned embodiment, and various modifications and applications can be made without departing from the spirit of the present invention. For example, although the medical treatment device is made of a non-magnetic metal so as to be used in an MRI system, the medical treatment device may be made of a magnetic metal so as to be used in an x-ray system.

REFERENCE SIGNS LIST

1: movable first electrode blade
2: fixed second electrode blade
3: turning shaft
4: electrode open/close rod connecting point
5: electrode open/close rod
6: coaxial cable
7: central electrode
8: external conductor
9: insulator
10: insulating portion
11: main body portion
12: connector
13: outer cylindrical tube
14: movable handle
15: turning element
16: coupling rod
17: insulator
101: movable first electrode blade
102: external conductor coupling portion
103: blade root portion
201: fixed second electrode blade
202: central electrode coupling portion
203: blade root portion

The invention claimed is:

1. A medical treatment device, comprising:
a coaxial cable for transmitting a microwave, wherein said coaxial cable comprises a central electrode and an external conductor;
a fixed second electrode blade provided on a front side of a distal end of said coaxial cable and connected to said central electrode, wherein said fixed second electrode blade comprises an electrode open/close rod connecting point;
a movable first electrode blade connected to said external conductor, wherein said movable first electrode blade comprises a turning shaft, and wherein said movable first electrode blade is configured to be turnable about said turning shaft and facing said fixed second electrode blade, and wherein manipulation of said movable first electrode blade is achieved at least in part by movement of said electrode open/close rod connecting point; and
a coupling rod for coupling said turning shaft and said electrode open/close rod connecting point to each other;
wherein said turning shaft of said movable first electrode blade is located on said movable first electrode blade side with respect to a center line of an edge line of said movable first electrode blade and an edge line of said fixed second electrode blade,
and wherein said electrode open/close rod connecting point is set on said fixed second electrode blade side with respect to the center line of the edge line of said movable first electrode blade and the edge line of said fixed second electrode blade; and
wherein said medical treatment device is configured to:
hold a living tissue between said movable first electrode blade and said fixed second electrode blade;
coagulate the living tissue by supplying a microwave; and
cut off the living tissue by turning said movable first electrode blade.

2. The medical treatment device according to claim 1, wherein an edge line of said movable first electrode blade and an edge line of said fixed second electrode blade are parallel to each other.

3. The medical treatment device according to claim 1 further comprising an insulator bonded to one surface of said fixed second electrode blade.

4. The medical treatment device according to claim 2, wherein a distance between said turning shaft of said movable first electrode blade and said electrode open/close rod connecting point is equal to or larger than the radius of said coaxial cable.

5. The medical treatment device according to claim 1, wherein said movable first electrode blade and said fixed second electrode blade are coated so as to prevent adhesion of a coagulated tissue.

6. The medical treatment device according to claim 1, wherein a clearance from a center of the distal end of said coaxial cable to a blade root portion of each of said movable first electrode blade and said fixed second electrode blade is equal to or larger than the radius of said coaxial cable, and wherein a clearance from a central electrode coupling portion to an external conductor coupling portion is equal to or larger than the radius of said coaxial cable.

* * * * *